United States Patent

Cutshall

[11] Patent Number: 5,231,700
[45] Date of Patent: Aug. 3, 1993

[54] PENETRATION RESISTANT HAND PROTECTOR

[75] Inventor: Tony A. Cutshall, Warsaw, Ind.

[73] Assignee: DePuy Inc., Warsaw, Ind.

[21] Appl. No.: 835,287

[22] Filed: Feb. 13, 1992

[51] Int. Cl.⁵ .............................................. A41D 19/00
[52] U.S. Cl. ....................................... 2/161.7; 2/167; 2/161.8
[58] Field of Search ............... 2/161 R, 167, 159, 169, 2/16, 163, 164; 57/216, 225 GD, 222, 210 GD, 226

[56] References Cited

U.S. PATENT DOCUMENTS

| | | | |
|---|---|---|---|
| 801,753 | 10/1905 | Ulrich | 2/161 R |
| 1,437,318 | 11/1922 | Kyle | 2/161 R |
| 4,004,295 | 1/1977 | Byrnes, Sr. | 2/161 R |
| 4,742,578 | 5/1988 | Seid . | |
| 4,777,789 | 10/1988 | Kolmes et al. . | |
| 4,779,290 | 10/1988 | Welch et al. | 2/167 X |
| 4,833,733 | 5/1989 | Welch et al. . | |
| 4,838,017 | 6/1989 | Kolmes et al. . | |
| 4,873,998 | 10/1989 | Joyner . | |
| 4,942,626 | 7/1990 | Stern et al. . | |
| 5,087,499 | 2/1992 | Sullivan | 2/167 X |

OTHER PUBLICATIONS

"For People Who Work on the Cutting Edge . . . ", Whizard ® Protective Wear Advertising, Occupational Hazards, p. 99, Jan. 1991.
"Protection . . . at your Fingertips.", Repel ® Cut Resistant Surgical Glove Liners Advertising, DePuy-DuPont Orthopaedics ™, pp. 1-2, 1990.
Perry ® Cut-Resistant Gloves Advertising, pp. 1-2, date unknown.
"Protection Without Sacrificing Precision", Centurion Surgical Glove Liners Advertising, Biomet, Inc., p. 1, date unknown.

Primary Examiner—Clifford D. Crowder
Assistant Examiner—Sara M. Current
Attorney, Agent, or Firm—Barnes & Thornburg

[57] ABSTRACT

A penetration resistant hand protector for medical applications comprising a glove having an exterior and an interior side. The glove also has stalls terminating with tip ends for four fingers and a thumb, a front palm side and a back side, and is formed from a cut resistant material. A puncture resistant covering is attached to at least two of the stalls of the four fingers and the thumb. The puncture resistance covering extends on the exterior side of tho glove to cover the fingers and thumbs on the palm side of the glove from at least the tip of the fingers to a point just below the attachment area of the finger to the palm of the hand so as to protect the fingers of the hand without inhibiting flexure of the palm portion of the glove. The cut resistant material is a composite formed from a resilient core and an outer winding of cut resistant fiber.

2 Claims, 2 Drawing Sheets

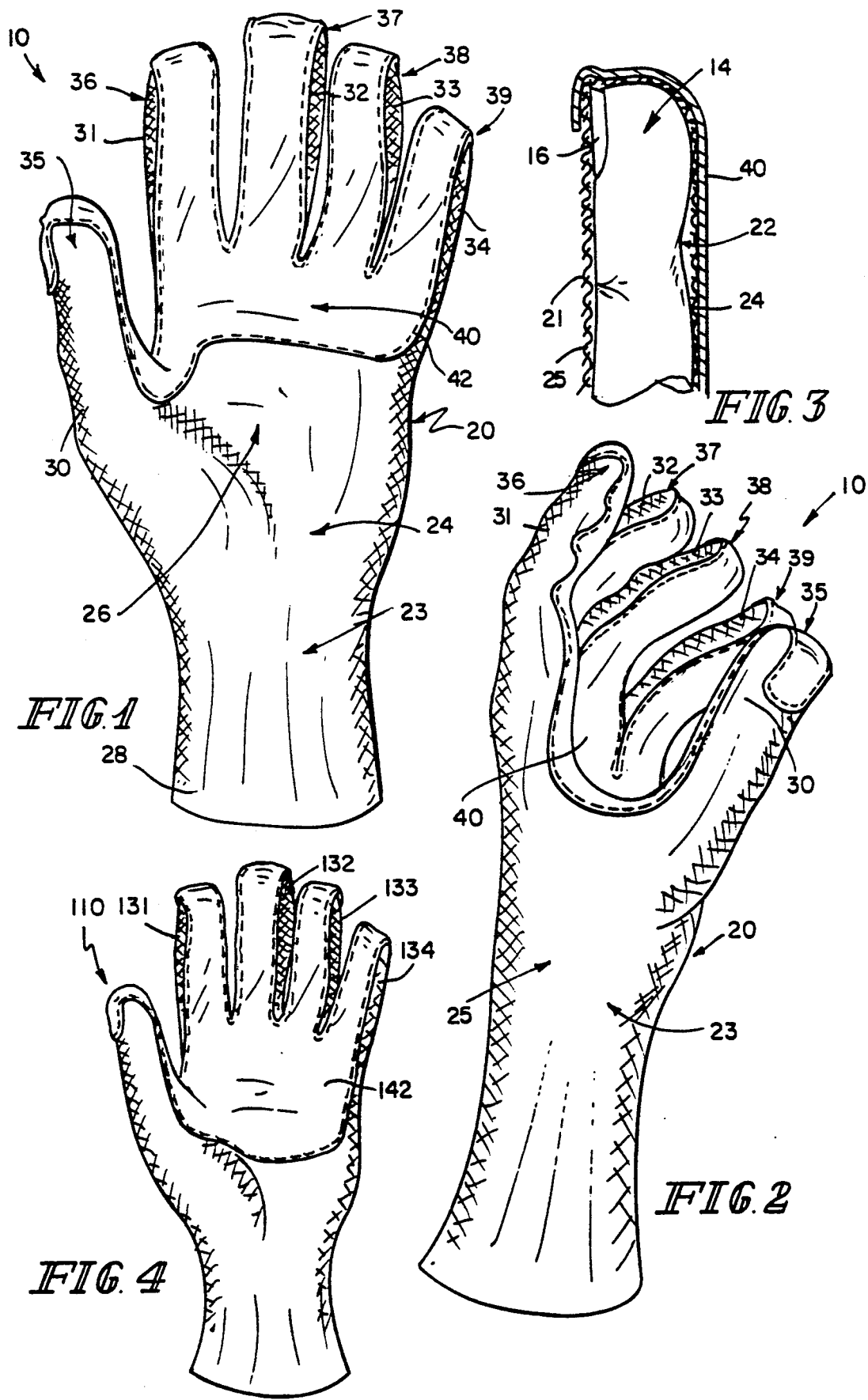

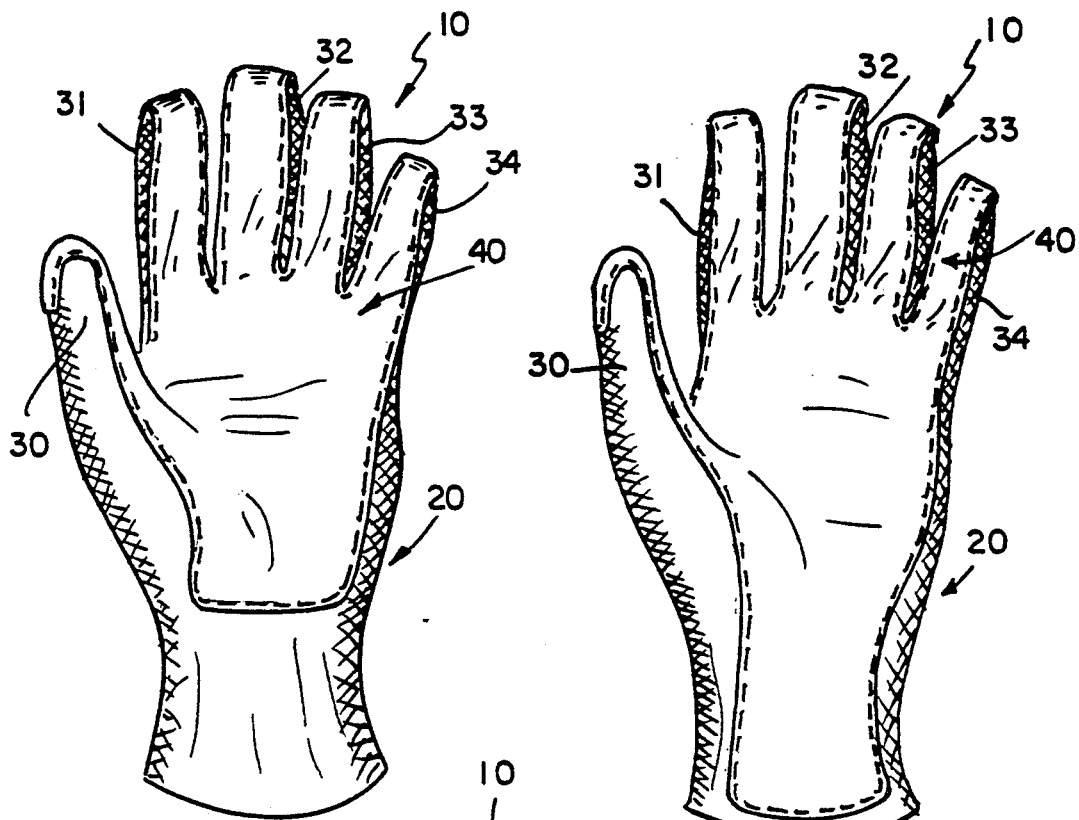
FIG. 5
FIG. 6
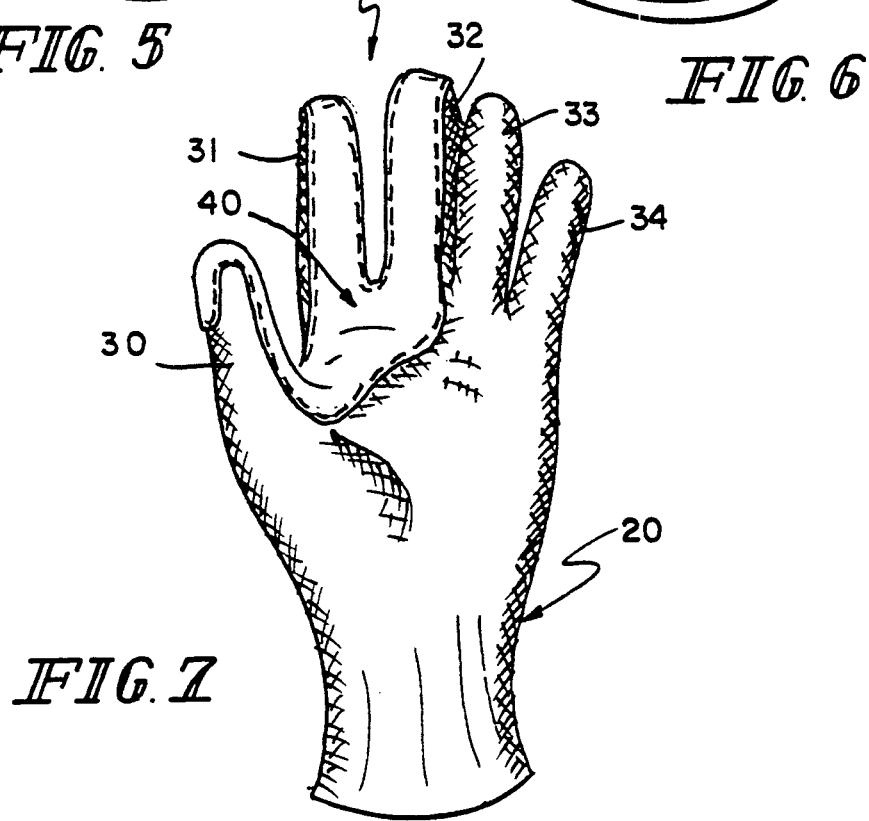
FIG. 7

PENETRATION RESISTANT HAND PROTECTOR

BACKGROUND AND SUMMARY OF THE INVENTION

The present invention relates to penetration resistant hand protectors for medical applications. More particularly, the present invention relates to puncture and cut resistant gloves for use by medical personnel.

Medical personnel are commonly placed in contact with a patient's body tissue, blood, and other body fluids. To minimize the risk of communicable disease transmission and introduction of foreign contaminants, protective hand gear is typically used during procedures that involve patient contact. Traditionally, medical personnel have used tight fitting latex gloves that prevent fluid contact between a patient and the hand. Latex gloves are inexpensive, effective for blocking fluid transfer, and widely available.

Proper protective hand gear is particularly critical for surgeons and surgical assistants working on trauma patients, or on patients requiring major reconstructive orthopedic surgery. Such operating environments are often filled with cutting implements, needles, bone fragments, and sharp bone edges, greatly enhancing the possibility of cutting through or puncturing traditional latex surgical gloves.

One method that has been used to reduce the chance of needle puncture is described in Stern et al., U.S. Pat. No. 4,942,626, which relates to a glove having a first discrete layer of flexible material having a pore size smaller than the diameter of a needle. This first layer is formed into a glove having openings in the fingerprint area of the index finger and little finger. A second discrete layer of flexible material, also having a pore size smaller than the diameter of the needle, is permanently attached to selected areas of the first layer. Generally, the selected areas include all of a thumb stall and lateral sides of both an index finger stall and middle finger stall, although col. 4, lines 61-65 disclose protection of all fingers and other hand locations deemed advisable. Although this type of needle-stick protective glove protects against needle-stick puncture of selected areas of a hand, significant protection against cutting lacerations of the hand is not provided.

Joyner, U.S. Pat. No. 4,873,998, describes a protective surgical hand covering equipped with a hardened mold material situated over selected regions of the hand. The hardened material covers portions of the palm, the knuckles, and the lower knuckles. Thimble-shaped tips formed of the hardened mold material can be placed over the fingers. Surgical latex gloves may be worn either over or under the protective surgical hand covering. Although this protective surgical hand covering protects against cuts to those areas directly covered by a hard mold material, those portions of the hand not covered by the hard mold material are still susceptible to cuts or punctures.

Seid, U.S. Pat. No. 4,742,578, describes a penetration resistant glove consisting of a thin latex of synthetic rubber foundation glove having a front surface overlay of a thin and pliable limp material. The thin, pliable material is composed of tightly interlaced fibers or filaments, typically interwoven high density nylon, that are adhesively attached to the face or palmar surface of the foundation glove. The surface overlay serves to prevent sharp object penetration. A hermetic seal can be formed over the combination foundation glove/pliable overlay by dipping in liquid latex rubber.

Welch et al., U.S. Pat. No. 4,833,733, describes a method for making a cut resistant surgical glove 10. The method includes the steps of dipping a mold shell 24 having the configuration of a human hand into a curable liquid 34. The curable liquid 34, when dried, must form a stretchable, air and water impermeable material. Prior to complete curing of the liquid 34, a hand shape layer of flexible armor fiber 18 is disposed on a dorsal side of the mold shell 24. The mold shell 24 is then dipped a second time into the liquid 34 to embed the armor fiber 18. Col. 3, lines 23-32 describe the use of aramid fibers such as Kevlar ®, manufactured by E.I. DuPont.

U.S. Pat. Nos. 4,777,789 and 4,838,017 to Kolmes et al. both describe cut resistant yarns used for manufacture of cut resistant garments. A yarn 10 as disclosed includes a core 12 formed from spun, monofilament, or multifilament fiber. Around the fiber core 12 is wrapped at least one strand of wire 22. The wire 22 is preferably annealed stainless steel wire.

Other protective hand wear is also known. For example, Bettcher Industries, Inc. produces Whizard ® Protective Wear, in which a combination of Spectra ®, Kevlar ®, and stainless steel yarn is knit to form laceration resistant products. Also, Smith and Nephew, Inc. produces Perry ® Cut-Resistant Gloves, formed from a continuous filament Spectra ® polyolefin fiber. Cut resistant surgical glove liners are manufactured by DePuy-DuPont Orthopaedics under the tradename Repel ®. The Repel ® surgical glove liners are made with Kevlar ® and Lycra ® materials.

The present invention provides a penetration-resistant hand protector for medical applications. The hand protector includes a glove having an exterior and an interior side. The glove is formed to allow a medical practitioner's hand to conformingly fit into contact with the interior side of the glove. The glove has stalls terminating in tip ends to accommodate all four fingers and thumb of a medical practitioner's hand. The glove has a front palm side, a back side, and is formed or woven from a cut-resistant material. A puncture-resistant covering is attached to at least two of the stalls of the four fingers and to the thumb stall.

In a preferred embodiment, the cut resistant yarn is a composite formed from a resilient core and an outer winding of cut resistant fiber. Generally, a continuous piece of cut resistant yarn is formed or woven to form the glove. The yarn may be a single continuous yarn. The puncture resistant covering is attached to the exterior of the glove and extends to cover the tip ends of the stalls of all four fingers as well as the thumb. In some embodiments, the puncture-resistant covering may also extend to cover part or all of the front palm side of the exterior of the glove, including the entire palmer surface. Optionally, the wrist may be covered in addition to covering of the palmer surface. These embodiments are particularly useful for trauma, orthopedic, or other surgical operations involving a substantial chance of puncture, cuts, or lacerations.

Additional features and advantages of the invention will become apparent to those skilled in the art on consideration of the following detailed description of preferred embodiments exemplifying the best mode of carrying out the invention as presently perceived.

BRIEF DESCRIPTION OF THE DRAWINGS

FIG. 1 is a front view of a penetration-resistant hand protector including a cut resistant glove configured to fit over a surgeon's hand and a puncture-resistant covering over selected areas of the cut resistant glove, the puncture resistant covering being attached to cover at least the palmer side of the finger and thumb stalls of the cut resistant glove;

FIG. 2 is a side view of the penetration resistant hand protector shown in FIG. 1, illustrating the extension of the puncture resistant covering over the finger and thumb tips;

FIG. 3 is a partially cut-away and closeup view of a surgeon's index finger encased by the penetration resistant hand protector illustrated in FIGS. 1 and 2;

FIG. 4 is a front view of an alternative embodiment of the invention in which a portion of the palmer surface of the glove is covered with a puncture-resistant covering;

FIG. 5 is a front view of an alternative embodiment of the invention in which the entire palmer surface of the glove is covered with a puncture-resistant covering;

FIG. 6 is a front view of an alternative embodiment of the invention in which the entire palmer surface and wrist of the glove is covered with a puncture-resistant covering; and FIG. 7 is a front view of an alternative embodiment of the invention in which only the stall of the index finger, middle finger, and thumb are covered with a puncture-resistant covering.

DETAILED DESCRIPTION OF THE DRAWINGS

A penetration-resistant hand protector 10 suitable for use in medical applications is shown in FIG. 1. The hand protector 10 includes a cut-resistant glove 20 formed to have an interior 22 and an exterior 23. The glove 20 has a front side 24 and a back side 25. The front side 24 is divided into several areas, including a palm covering 26 dimensioned to fit over a palm (not shown) of medical practitioner. A medical practitioners wrist is protected against cuts and lacerations by a wrist covering 28. In addition, the wrist covering 28 can be configured to elastically engage the wrist of a medical practitioner, helping to retain the glove 20 on the hand.

The index, middle, ring, and little finger of the hand of the medical practitioner (not shown) fit respectively into an index finger stall 31, a middle finger stall 32, a ring finger stall 33, and a little finger stall 34. The thumb fits into the thumb stall 30. Each stall 30, 31, 32, 33, and 34 respectively terminate in thumb tip 35, an index finger tip 36, a middle finger tip 37, a ring finger tip 38, and a little finger tip 39.

The cut resistant glove 20 may be made available in a range of sizes to accommodate differently sized hands. To aid in quick determination of the correct size, the cut resistant glove can be marked with size indicators (eg. printing small, medium, large, extra large on the glove 20), or sizes can be indicated by color coding of the glove 20 of selected regions of the glove. In one preferred embodiment the wrist covering 28 is colored white for small sized gloves, yellow for medium sized gloves, blue for large sized gloves, and red for extra large sized gloves.

Although the illustrated wrist covering 28 only covers the carpal region of a medical practitioner, in alternative contemplated embodiments the wrist covering 28 can be extended to cover at least some portions of the forearm of a medical practitioner. Alternatively, the wrist covering 28 can be reduced or entirely absent if protection of the carpal area is not necessary.

The cut resistant glove 20 is woven of a cut-resistant yarn 21 (indicated in FIG. 3). The cut-resistant yarn 21 may be formed as a composite material having a resilient core and an outer winding of cut-resistant fiber. The resilient core can be an elastic fiber such as Lycra ®, manufactured by E. I. Dupont, Inc. and the outer winding can be an aramid fiber such as Kevlar ®, also manufactured by E.I. Dupont, Inc. As compared to cotton, latex, or leather gloves, a glove 20 constructed of a Kevlar ®/Lycra ® composite has a far superior cut resistance. Preferably, a continuous yarn of the composite cut-resistant yarn 21 is used.

Alternatively, it is contemplated to construct the cut resistant glove 20 from other synthetic fibers, preferably high strength, lightweight fibers that can be used alone or in composite yarns. Nylon, polyolefins, or other conventional fibers known in the art are contemplated. In addition, composites of metal and synthetics may be used. It should be noted that synthetic materials are desirable to manufacture the glove 20, since gloves constructed from woven steel or other metallic wire unduly sacrifice manual dexterity and sensitivity, while greatly increasing the cost of the glove. Since the glove 20 is typically intended for single use followed by disposal as medical waste, low cost manufacture is essential.

Although the glove 20 provides protection against cutting or lacerating wounds, needles or other pointed, puncturing objects (eg. bone chips) may slip between the woven yarn. To increase resistance to punctures, a puncture-resistant covering 40 is attached to cover selected areas of the exterior 23 of the cut-resistant glove 20. The puncture resistant covering 40 is preferably constructed from a single layer of processed animal hide, such as calfskin, buckskin, cabretta leather, or other soft and supple type of leather. In the illustrated embodiment, the covering 40 is made from processed deerskin. However, further variations would include coverings of polymers, synthetic leather-like material, pliant metals, or natural elastomers. Although leather does not have a great deal of resistance to cutting action, it is highly resistant to punctures.

As best shown in FIG. 1, the puncture-resistant covering 40 is attached with thread stitching 42 to the index finger stall 31, the middle finger stall 32, the ring finger stall 33, the little finger stall 34, and the thumb stall 30. The puncture resistant covering 40 is wrapped over the fingertips 35, 36, 37, 38, and 39 and, as best seen for example in FIG. 3, terminates on the back side 25 over a nail 16 of a finger tip 14 of a medical practitioner. This attachment arrangement protects those areas of the fingers or thumb most likely to suffer needle puncture during surgical operation.

As shown in FIG. 1, the puncture resistant covering 40 extends to cover at least a portion of the palm covering 26. As shown in FIG. 1, the portion of the palm covering 26 normally positioned over the interdigital pads of a medical practitioner is protected against needle puncture. As shown in FIGS. 1, 4–7, the puncture resistant covering 40 can optionally cover any or all of the thumb stall 30, finger stalls 31, 32, 33, 34, interdigital pads, palmer surface of the hand, wrist and forearm, or portions thereof. In alternative embodiments, at least a portion of the back side 25, can also be protected by a puncture resistant covering.

As will be appreciated by those skilled in the art, various changes and modifications may be made without departing from the scope and spirit of the invention as defined by the following claims:

I claim:

1. A penetration resistant hand protector for medical applications, the hand protector comprising
   - a glove having an exterior and an interior side, formed to allow a medical practitioner's hand to conformably fit into contact with the interior side of the glove, the glove having stalls terminating with tip ends for four fingers and a thumb, a front palm side and a back side, and formed from a cut resistant material,
   - a puncture resistant covering attached to at least two of the stalls of the four fingers and the thumb,
   - wherein the puncture resistant covering extends on the exterior side of the glove to cover the fingers and thumb on the palm side of the glove from at least the tip of the fingers to a point just below the attachment area of the finger to the palm of the hand so as to protect the fingers of the hand without inhibiting flexure of the palm portion of the glove,
   - wherein the cut resistant material is a composite formed from a resilient core and an outer winding of cut resistant fiber,
   - wherein the outer winding of cut resistant fiber is aramid fiber, and
   - wherein the glove is made from a continuous material.

2. The hand protector of claim 1, wherein the wrist portion of the glove is color coded to indicate glove size.

* * * * *